United States Patent [19]

Varshavsky

[11] 4,442,203

[45] Apr. 10, 1984

[54] GENE AMPLIFICATION ASSAY FOR DETECTING TUMOR PROMOTERS

[75] Inventor: Alexander J. Varshavsky, Cambridge, Mass.

[73] Assignee: Massachusetts Institute of Technology, Cambridge, Mass.

[21] Appl. No.: 279,155

[22] Filed: Jun. 30, 1981

[51] Int. Cl.$^3$ .......................... C12Q 1/68; C12Q 1/00
[52] U.S. Cl. ............................................. 435/6; 435/4
[58] Field of Search .......................... 435/6, 29, 4, 172

[56] References Cited

U.S. PATENT DOCUMENTS

| | | | |
|---|---|---|---|
| 4,066,510 | 1/1978 | Thilly | 435/29 X |
| 4,072,574 | 2/1978 | Loeb et al. | 435/6 |
| 4,256,832 | 3/1981 | Findl et al. | 435/29 X |
| 4,299,915 | 11/1981 | Thilly et al. | 435/6 |
| 4,302,535 | 11/1981 | Skopek et al. | 435/29 X |
| 4,307,189 | 12/1981 | Kit | 435/6 |
| 4,345,026 | 8/1982 | Lew | 435/29 X |

OTHER PUBLICATIONS

A. Varshavsky, Proc. Natl. Acad. Sci. U.S.A., vol. 78, No. 6, pp. 3673–3677, 1981.
A. Varshavsky, Cell, vol. 25, pp. 561–572, 1981.

*Primary Examiner*—Robert J. Warden
*Attorney, Agent, or Firm*—Arthur A. Smith, Jr.; David E. Brook

[57] ABSTRACT

A correlation between gene amplification and tumor promotion is disclosed herein. This correlation allows for a simple cellular assay that indicates whether a substance or process is a tumor promoter. This assay does not depend upon numerous biochemical processes that introduce uncontrolled and unascertained varibles into other cellular assays. This assay can also be used to determine whether a set of cells is abnormally genetically labile and therefore susceptible to cancer or genetic disease.

11 Claims, 1 Drawing Figure

GENE AMPLIFICATION ASSAY FOR DETECTING TUMOR PROMOTERS

TECHNICAL FIELD

This invention is in the fields of biology and chemistry.

BACKGROUND ART

The nature and causes of cancer are not entirely understood. In general, it is believed that cancer may be caused when one or more cells are genetically transformed in some manner which hinders or removes the normal limitations on the reproductive capacity of the cells [1, 2]. If the transformed genetic structure is inherited by descendant cells, the cells undergo uncontrolled proliferation, which is characteristic of malignant tumors.

The biochemical substances and processes involved in genetic replication are very complex, and relatively minor variations may result in substantial or extreme alterations in the descendant cells [3, 4, 5].

In general, tumor formation is believed to be a two-stage process. The initial event of carcinogenesis is called "initiation," which involves the transformation of a cell into a "pre-cancerous" cell. The following stage is called "promotion," which involves the proliferation and possible evolution of the transformed cell, thereby creating a tumor. Numerous substances and processes are believed to enhance the initiation or the promotion of cancerous cells. These substances and processes are usually referred to as "carcinogens" and "tumor promoters," depending upon whether their predominant effect relates to the initiation or the promotion of tumors.

In general, a carcinogen is a substance or process which, when exposed to cells, increases the rate or probability of genetic transformation of the cells or their descendants, resulting in the emergence of cells capable of forming tumors [6, 7]. Carcinogens are believed to include viruses [8], chemical substances [9], and radiation [10].

A tumor promoter is a substance which, when exposed to cells in combination with one or more carcinogens, significantly increases the size or incidence of tumors [11, 12]. To determine whether a suspected tumor promoter is active mainly during the promotion stage, the substance may be administered to an animal without additional administration of a carcinogen; a low incidence of tumors indicates a low level of carcinogenicity.

Both carcinogens and tumor promoters may be somewhat cytotoxic; i.e., at sufficiently high concentrations, they may kill cells directly, thereby preventing them from reproducing. In addition, carcinogens may have some degree of tumor-promoting capacity, and tumor promoters may have some degree of carcinogenicity.

A common procedure for measuring the tumor-promoting characteristic of a substance or process is to administer the substance or process to an animal in combination with a carcinogen that has a known level of carcinogenicity. For example, in one common experimental protocol [13], the backs of numerous mice are shaved, and the mice are divided into two categories, one of which serves as a control group. A predetermined quantity of a known carcinogen is administered to the backs of the control-group mice. This same amount of carcinogen, plus a predetermined quantity of a suspected tumor promoter, are administered to the backs of the other group of mice. If the doubly-exposed mice develop a significantly higher incidence of tumors on their backs, the suspected substance is regarded as a tumor promoter. For example, a class of substances known as phorbol esters is known to contain several substances that are tumor promoters. In particular, 12-O-tetradecanoylphorbol--13-acetate (TPA) has been shown by mouse skin assays to be a very potent tumor promoter. When a relatively low dose of dimethylcholantren was applied alone to mouse skin, the incidence of tumors was approximately six percent. However, when both TPA and the same dose of dimethylcholantren were applied to mouse skin, the incidence of tumors increased to nearly 100 percent [14].

This experimental procedure suffers several limitations and drawbacks, including the following:

1. It is time-consuming. It may require several weeks or months for all incipient tumors to develop, depending upon the carcinogenicity of the substances administered.

2. It is expensive. Even the simplest and most common laboratory animals, such as common mice, are relatively expensive to procure and properly feed and care for. Special lines of mice with various desired characteristics are often extremely expensive. Research involving higher mammals such as dogs, pigs, and primates is often necessary, and is correspondingly more expensive.

3. Research involving animals is less reproducible, and is more subject to extraneous variables that cannot be entirely eliminated or predicted. Since only a limited number of animals may be used for a given experiment, small variations (e.g., deaths because of extraneous factors) can cause significant variations in the results. By contrast, millions of cells may be used quickly and inexpensively in a cellular assay.

4. Research involving animals requires far more space than research involving cells. In biological research laboratories, space is valuable and expensive.

For these reasons, it is very desirable and useful to measure the tumor promoting potential of a substance or process by assays involving cultures of cells, rather than animals.

A variety of cellular assays involving TPA and other tumor promoters have shown that tumor promoters induce a wide-range of metabolic effects, including stimulation of macromolecular metabolism and cell growth [17], alteration of various plasma membrane functions such as phospholipid metabolism [18] and sugar transport [19], suppression or enhancement of terminal differentiation [20], induction of viral antigens, [21] and altered cellular morphology [22]. However, none of these assays is necessarily directly related to genetic transformation of cells; in addition, other assays have shown that TPA does not display mutagenic activity in conventional mutation assays [23]. Therefore, such assays may not provide a reliable indication of whether a substance or process can promote tumors or other genetic transformation.

A different type of assay has been separately developed to determine gene amplification. This assay has been used to study the causes and characteristics of cellular resistance to drugs. One such assay involves methotrexate (MTX), a cytotoxic drug. MTX kills cells by binding very tightly to an enzyme, dihydrofolate reductase (DHFR). A single molecule of DHFR enzyme is inactivated by a single molecule of MTX. Since DHFR is essential to the metabolism and reproduction of a cell, a cell that contains a normal quantity of DHFR molecules may be killed by a predetermined quantity of MTX. However, some cells produce higher quantities of DHFR than do other cells. These cells may have enough DHFR to resist and survive exposure to a given concentration of MTX, and to reproduce. It has been shown that MTX resistance, which is due to abnormally high quantities of DHFR, is primarily due to amplification of the DHFR locus of the DNA molecule. In other words, in MTX-resistant cells, the portion of DNA that codes for the production of the DHFR enzyme is repeated an abnormally high number of times either within the chromosome or as extra-chromosomal DNA [24].

Methotrexate is not the only selective agent that can be used to assess gene amplification. For example, several heavy metals such as cadmium are cytotoxic. These metals can be bound and inactivated by certain proteins, such as metallothionein. Therefore, cells that have an abnormally high quantity of metallothionein are more likely to survive exposure to heavy metals such as cadmium. The presence of abnormally high quantities of metallothionein or similar enzymes is indicated by resistance to cadmium or similar selective agents. The correlation of such resistance to gene amplification, rather than to induced transcription or translation, has been demonstrated [25]. Similarly, the addition of phosphonacetyl-L-aspartate to a cell culture kills cells that do not have an abnormally high quantity of loci that code for a multifunctional protein referred to as CAD [26]. In general, an enzyme or other biological substance that is bound, inactivated, destroyed, or otherwise altered by a drug or other substance is regarded as a "target" of that substance.

Mutations and genetic transformations that are induced by carcinogens or mutagens are presumed to occur randomly within the cellular genome. Therefore, amplification of a single genetic locus, such as the DHFR locus, is presumed to be representative of amplification of numerous other loci as well. The number of copies of a certain type of locus within a cell may be determined through the use of radioactive "probes" by using a process known as "dot hybridization" [27]. This assay can be used to support the interpretation that an abnormally high quantity of an enzyme is caused by gene amplification, rather than by activation of transcription or translation.

DISCLOSURE OF THE INVENTION

This invention relates to a gene-amplification assay that indicates the tumor promoting potential of a substance or process. A correlation has been discovered between gene amplification and tumor promotion. This correlation allows for a simple, inexpensive cellular assay that provides valuable information regarding whether a substance or process has tumor-promoting characteristics.

In this assay, a culture of human or other mammalian cells is divided into two categories, one of which serves as the control. The control population is exposed to a substance such as methotrexate (MTX), which acts as a gene-amplification selective agent. The number of cells that survive exposure to the selective agent is counted. The other population is exposed to a suspected tumor promoter, and to the same selective agent to which the control population was exposed. If the number of cells that survive the double exposure significantly exceeds the number of singly-exposed control cells that survive, the higher survival rate indicates that the suspected tumor promoter is in fact a tumor promoter.

This cellular assay allows for the investigation of suspected tumor promoters using methods that are less time-consuming, less expensive, more stochastically determinable, and which require less space than conventional assays involving the induction of tumors on animals. In addition, this assay, which focuses upon gene-amplification, eliminates or reduces several variables, such as the rates of transcription or translation, that prevent other cellular assays from providing accurate and reliable information regarding the tumor promoting capacity of a substance or process.

BEST MODE OF CARRYING OUT THE INVENTION

Figure 1:
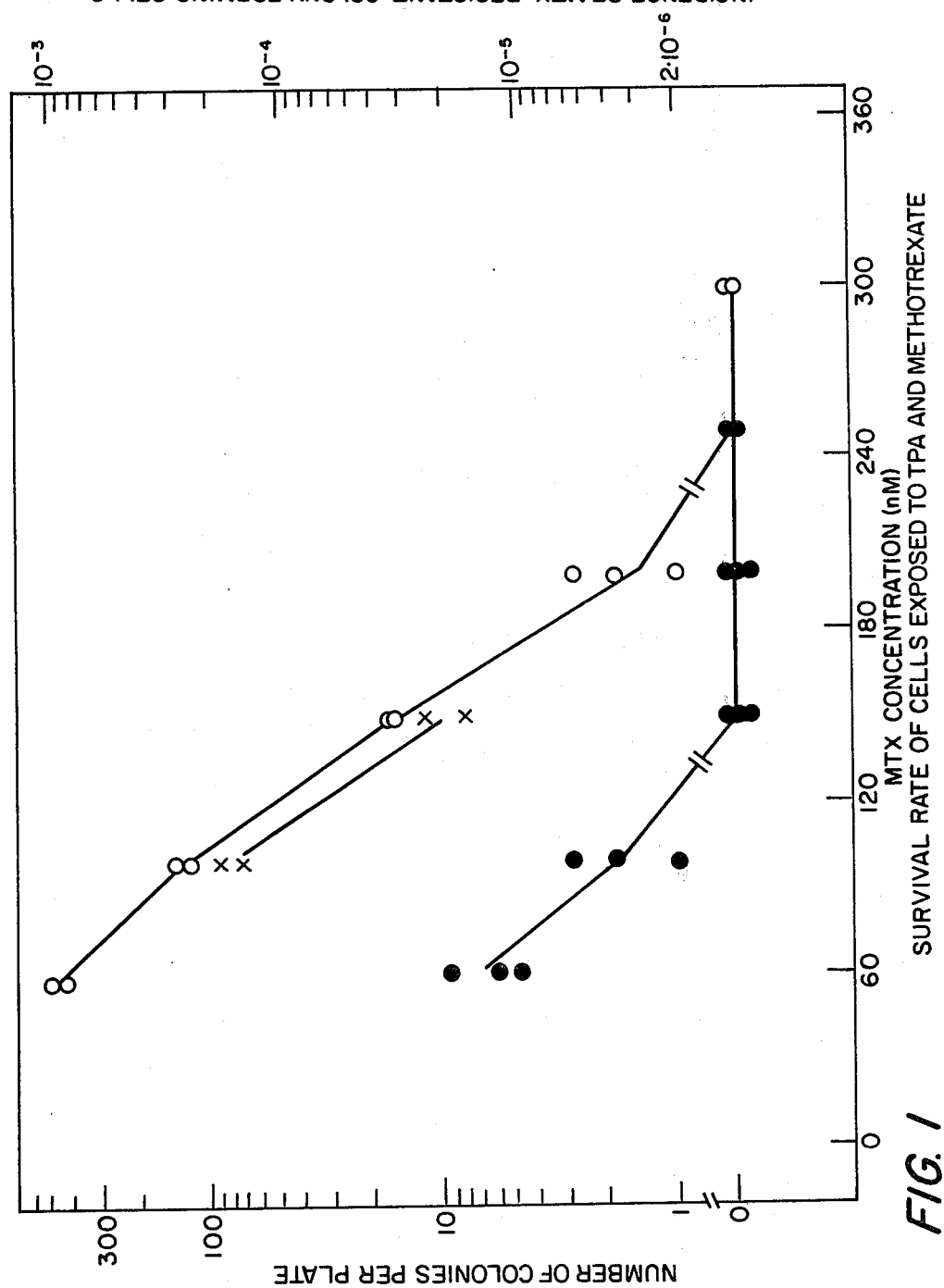
FIG. 1 is a graph indicating the survival of cells exposed to TPA and Methotrexate.

This invention relates to the experimental observation that a correlation exists between a common assay involving animals, and a faster and more useful cellular assay. Therefore, the first embodiment of this invention described below comprises an experiment to determine the effect of a tumor promoter, the characteristics of which have been previously determined by animal studies, upon cells in culture. The second embodiment described below comprises the typical procedures that could be used in a cellular assay to indicate whether a substance is a tumor promoter. The third embodiment of this invention relates to the use of this assay to determine whether a cell population is abnormally genetically labile and therefore susceptible to cancer, genetic disease, or other genetic transformation.

A first preferred embodiment of this invention involved the effect of TPA, a known tumor promoter, on a colony of cells. Mouse fibroblast cells of a 3T6 line were grown to a confluent monolayer on a 10 cm plate. The cells were detached from the plate using trypsin, and a homogenized suspension of cells was created. The concentration of cells in suspension was determined, and a known quantity of cells was administered to each of three 10 cm petri dishes. Plate 1 was exposed to 0.1 ug/ml of TPA.

After the cells had grown for approximately six generations on plates 1, 2 and 3, all three plates were exposed to 200 nM MTX. Plates 1 and 2 were also exposed to 0.1 ug/ml TPA. The incidence of surviving, MTX-resistant cells in plate 3 (control; no TPA) was about $5 \times 10^{-7}$ (i.e., about 2 survivors per $10^6$ cells). The incidence of MTX-resistant cells in plate 2 (TPA simultaneous with MTX) was approximately $200 \times 10^{-7}$. The incidence of MTX-resistant cells in plate 1 (TPA prior to and concurrent with MTX) was approximately $500 \times 10^{-7}$. These results indicated that TPA, a known tumor promoter, increased the rate of DHFR gene amplification by a factor of up to 100 fold, as shown in FIG. 1.

A similar experiment was conducted using phorbol instead of TPA. Phorbol is chemically similar to TPA, but it has been shown by animal studies not to be a tumor promoter. Exposure to phorbol did not increase the rate of cell survival in MTX, which indicates that phorbol does not tend to cause gene amplification. Additional similar experiments performed using substances known to have intermediate levels of tumor-promoting activity indicated that those substances tend to cause intermediate levels of gene amplification, as shown on Table 1, and described in Example 3. These results indicate that tumor promoters tend to cause gene amplification, and that a cellular gene amplification assay can be used to determine whether a substance or process is a tumor promoter.

A second preferred embodiment of this invention comprises the procedures that could be used to conduct a cellular assay that indicates whether a substance is a tumor promoter. In this embodiment, a culture of cells is divided into two subpopulations. One subpopulation is exposed to a first substance which is suspected of being a tumor promoter. That subpopulation is also exposed to a second substance, such as MTX, which measures the incidence of gene amplification at a certain chosen locus. The other subpopulation, which serves as a control, is exposed to the second substance, but not to the suspected tumor promoter. If the number of survivors in the first population is substantially higher than the number of survivors in the control population, the substance should be regarded as a tumor promoter. It may be so classified, or it may become the subject of subsequent animal experiments to confirm the belief that it is a tumor promoter.

A third preferred embodiment of this invention involves a gene-amplification assay to determine whether a cell or group of cells is genetically labile, i.e., phenotypically or genetically unstable. This assay could be used to detect a variety of genetic diseases, such as Bloom's syndrome. In addition, this assay could be used to detect the level of stress that has been or is being imposed on the DNA of a cell or group of cells, for example, as an indication of the extent to which a smoker's lung fibroblastic cells are susceptible to cancer. In this embodiment, the cells of interest are divided into two subpopulations. One subpopulation is exposed to a substance such as MTX, which measures gene amplification. The other subpopulation is exposed to MTX, as well as to a known gene-amplifier such as TPA. The rate of survival of each population to MTX exposure is compared, to determine the extent to which TPA induces gene-amplification in the cells being examined. The same procedure under identical conditions is performed on two subpopulations of normal reference cells to determine a basal level of gene amplification. The incidence of induction of gene amplification by each type of cell is then compared. If the cells being examined are induced to gene amplification at a higher rate than the normal cells, this indicates that the cells being examined tend to be genetically labile and more susceptible to cancer.

An alternate version of this third preferred embodiment may be used to assess genetic lability and susceptibility to cancer, genetic disease, or other genetic transformation, without requiring the use of known or suspected tumor promoters. In this assay, a population of suspected cells and a population of control cells are exposed to a substance which selects for gene amplification, such as MTX. If a significantly higher number of cells in the suspected population survive exposure to MTX, this indicates that the suspected cells tend to be genetically labile, and susceptible to cancer, genetic disease, or other genetic transformation.

None of these embodiments is restricted to any specific strain, line, or type of cell. The work performed to date has used mammalian fibroblast cells; however, research utilizing the methods of this invention with other types of cells may prove that other types of cells provide valuable information regarding gene amplification and tumor promoting effects of a variety of substances and processes.

EXAMPLES

Example 1: Cells and Reagents Used

Mouse fibroblast cells of the 3T6 line [28] were grown in Eagle's minimal essential medium (Grand Island Biological Company (GIBCO), New York), supplemented with penicillin (50 $\mu$g/ml), streptomycin (50 $\mu$g/ml), sodium pyruvate (110 $\mu$g/ml), $Fe(NO_3)_2$ (300 nM), glucose (1.5 g/l) and 11% dialyzed calf serum. Dialyzed serum was obtained from GIBCO and additionally dialyzed at 4° C. against 50 volumes of 0.14 M NaCl, 1 mM $Na_2HPO_4$ (pH 7.0) for 3 days. Cells were grown in Falcon tissue culture plates, 10 cm diameter, at 37° C. in 5% $CO_2$ - 95% air at 98% relative humidity. Cells were grown to confluent monolayers, detached with trypsin (GIBCO) and removed from the initial culture plates. The cellular suspension was then made uniform by vigorous pipetting. Cell numbers in suspension were determined by a hemocytometer (Neubauer's improved chamber, American Scientific Products, Boston) and occasionally confirmed by a Coulter cell counter, so that a known number of cells could be seeded onto a plate by addition of a known volume of suspension.

For staining, the medium was decanted from the plate and replaced for 30 min at room temperature with 10% formaldehyde, 0.14 M NaCl, 5 mM triethanolamine-HCl (pH 7.0). The formaldehyde solution was decanted, and the plate gently rinsed with $H_2$ followed by staining with Gill's hematoxylin No. 3 (Fisher Scientific Co., Boston) for 10-15 min. Stained colonies were scored using a 10X optical comparator and in ambiguous cases verified with an inverted microscope.

Methotrexate (MTX) was obtained from Sigma Chemical Co., St. Louis. Stock MTX solutions were made in $H_2O$ with 0.1 M NaOH added to adjust pH to 7.5, sterilized by filtration and stored at $-20°$ C. TPA, phorbol, phorbol 12,13-diacetate (PDA), and phorbol 12,13-dibutyrate (PDB) were obtained from Consolidated Midland Corporation (Brewster, N.Y.). Their stock solutions (5 mg/ml) were prepared in reagent grade dimethylsulfoxide (DMSO) and stored at $-70°$ C.

Example 2: Gene Amplification by TPA

Numerous Falcon culture plates were seeded with $5 \times 10^5$ cells per plate. The plates were divided into three categories, indicated in FIG. 1. The solid circles indicate control plates, which were exposed to MTX at the concentrations shown, but were not exposed to TPA. The plates indicated by open circles were exposed to TPA at 0.1 $\mu$g/ml for six generations prior to exposure to MTX in the concentrations indicated; TPA exposure was continued during MTX exposure. The plates indicated by x's were exposed to 0.1 $\mu$g/ml and simultaneously to MTX at the concentrations indicated. The plates were incubated for a sufficiently long time for MTX-sensitive cells to detach and die, and for MTX-resistant cells to grow and form colonies; this period of time range from 10 to 30 days, and averaged about 20 days. The number of MTX-resistant cells at each MTX concentration was then determined by counting the colonies which these cells gave rise to. As indicated in FIG. 1, exposure to TPA increased the number of MTX-resistant cells by a factor of almost 100 times. For example, at 100 nM MTX, between 1 and 3 colonies per plate are formed in the absence of TPA, whereas in the presence of TPA about 90 colonies per plate were formed. The number of colonies per plate is shown on the left vertical axis; the incidence of resistant cells, shown on the right axis, is determined by dividing the number of colonies by the initial seeding density, $5 \times 10^5$ cells/plate.

Example 3: Effect of Intermediate Tumor Promoters on Gene Amplification

Both phorbol 12,13-diacetate (PDA) and phorbol 12,13-dibutyrate (PDB) have been shown by animal tests to have intermediate levels of tumor-promoting activity [29]. Both of these substances were tested for gene amplification according to the procedures of Example 1. The results, indicated in Table 1, indicate that these substances exhibit intermediate levels of gene amplication activity.

TABLE 1

Correlation Between Tumor Promoting Activity and Gene Amplication Activity

| Exposure | Number of surviving colonies per plate | Incidence of MTX-resistant, colony-forming cells |
|---|---|---|
| 200nM MTX | 0.66 | $3.3 \times 10^{-7}$ |
| Phorbol + MTX | 1 | $5.0 \times 10^{-7}$ |
| PDB + MTX | 16 | $8.0 \times 10^{-6}$ |
| PDA + MTX | 20 | $1.0 \times 10^{-5}$ |
| TPA + MTX | 61 | $3.0 \times 10^{-5}$ |

Example 4: Absence of Gene-Amplification Effect of Non-Tumor Promoters $2 \times 10^6$ cells were seeded onto each of numerous plates. The plates were exposed to varying concentrations of phorbol (a structural analog of TPA), DMSO (the solvent used to dissolve all of the tumor promoters), or thymidine (a substance which promotes cell survival in the presence of MTX) simultaneously with exposure to 200 nM MTX. As indicated in Table 2, although TPA had a marked effect upon the incidence of MTX-resistant cells, neither phorbol, nor DMSO, nor thymidine had any similar effect.

INDUSTRIAL APPLICABILITY

The invention described herein has industrial applicability in the identification of tumor-promoting substances and processes. Such identification is necessary to prevent or control their entry into the environment, and to determine cost-effective methods of reducing the incidence of cancer. In addition, this invention can be used to indicate whether a cell population is genetically labile and therefore susceptible to cancer, genetic disease, or other genetic transformation. Such analyses can be used to prevent birth defects and to identify and commence preventive remedial action for people who are susceptible to cancer.

EQUIVALENTS

Those skilled in the art will recognize, or be able to determine using no more than routine experimentation, many equivalents to the specific procedure described herein. Such equivalents are considered to be within the scope of this invention and are intended to be covered by the following claims.

REFERENCES

1. H. H. Hiatt et al, *Origins of Human Cancer* (Cold Spring Harbor Lab) 1977.
2. G. Klein, *Viral Oncology* (Raven Press, New York) 1980.
3. A. Lehninger, *Biochemistry*, 2d ed., p. 859 et seq., (Worth Publ., New York) 1975.
4. A. Kornberg, *DNA Replication* (Freeman & Co., San Francisco), 1980.
5. L. Stryer, *Biochemistry*, 2d ed. (Freeman & Co., San Francisco), 1981.
6. Hiatt, supra note 1, at pages 605–629.
7. J. H. Weisburger et al, in *Toxicology*, p. 84–138, by J. Dowell et al, MacMillan Publ. NYC 1980.
8. Klein, supra note 2.
9. Weisburger, supra note 7.
10. Hiatt, supra note 1, at pages 923–841.
11. Hiatt, supra note 1, at pages 751–784.
12. W. G. Thilly et al, *Toxicology*, supra note 7, pages 139–157. 13. See, e.g., E. Hecker, *Methods in Cancer Res.* 6: 439–484 (1970); R. K. Boutwell, *C.R.C. Crit. Rev. Toxicol.* 2: 419–443 (1974).
14. R. K. Boutwell, *C.R.C. Crit. Review Toxicol.* 2:419–443 (1974).
15. L. Ossowski et al, *J. Biol. Chem.* 249: 4312–4320 (1974); M. Wigler et al, Nature 359: 232–233 (1976).
16. I. B. Weinstein et al, *Carcinogenesis*, (D. Reidel Publ.) 1980; L. Diamond et al, *Adv. Cancer Res.* 32 (1980).
17. Boutwell, supra note 14, at pages 607–612.
18. V. Kinsel et al, *Cancer Res.* 39: 2743–2756 (1979).
19. P. E. Driedger et al, *Cancer Res.* 37: 3257–3265 (1977).
20. R. K. Stuart et al, *Science* 208: 402–404 (1980); S. Mondal, *Cancer Res.* 40: 334–338 (1980).
21. S. K. Arya, *Nature* 284: 71–72 (1980).
22. L. Diamond, *Adv. Cancer Res.* 32: 1–63 (1980).
23. L. M. Thompson et al, *Cancer Res.* 40: 3245–3251 (1980): J. E. Trosko et al, *Cancer Res.* 37: 188–193 (1977).
24. R. T. Schinke, *Scientific American* 243: 60–69 (Nov. 1980).
25. L. R. Beach et al, *Proc. Natl. Acad. Sci. USA* 78: 2110–2114 (1981).
26. G. M. Wahl et al, *J. Biol. Chem.* 254: 8679–8689 (1979).
27. F. C. Kafatos et al, *Nucleic Acids Res.* 7: 1541–1552 (1979); P. S. Thomas, *Proc. Natl. Acad. Sci. USA* 77: 5201–5205 (1980); S. Weisbrod et al, *Cell* 23: 391–400 (1981); J. H. Nunberg et al, Cell 19: 355–364 (1980).
28. G. J. Todaro, *J. Cell Biol.* 17: 299–313 (1963).
29. L. Diamond, *Adv. Cancer Res.* 32: 1–63 (1980).

I claim:

1. A method for indicating the tumor-promoting characteristics of a substance or process, comprising determining the incidence of gene amplification of a cell culture that is induced by said substance or process and using the induction of gene amplification as an indication of the tumor-promoting capability of the substance or process.

2. A method of claim 1 wherein said incidence of gene amplification is determined by a process comprising the following steps:

a. dividing said cell culture into at least one first group of cells and at least one second group of cells;
b. contacting said first group with said substance or process;
c. contacting said first group and said second group with a second substance that kills cells which do not have a relatively high number of copies of at least one DNA locus that codes for the production of a protein that is the target of said second substance;
d. determining the incidence of cells in each of said groups that survive the contact with said second substance;
e. comparing the number of surviving cells in each of said groups to determine whether the substance or process affects the incidence of gene amplification; and,
f. determining the tumor promoting characteristics of said substance or process from its affect upon the incidence of gene amplification.

3. A method of claim 2 wherein said second substance is selected from the following group: methotrexate, heavy metals, and phosphonacetyl-L-aspartate.

4. A method for indicating the tumor-promoting characteristics of a substance or process, comprising the following steps:
a. dividing said cell culture into at least one first group of cells and at least one second group of cells;
b. contacting said first group with said substance or process;
c. contacting said first group and said second group with a second substance that kills cells which do not have a relatively high number of copies of at least one DNA locus that codes for the production of a protein that is the target of said second substance;
d. determining the incidence of cells in each of said groups that survive the contact with said second substances;
e. comparing the number of surviving cells in each of said groups to determine whether the substance or process affects the incidence of gene amplification; and,
f. determining the tumor promoting characteristics of said substance or process from its affect upon the incidence of gene amplification.

5. A method of claim 4 wherein said second substance is selected from the following group: methotrexate, heavy metals, and phosphonacetyl-L-aspartate.

6. A method for indicating whether cells are abnormally genetically labile, comprising the following steps:
a. determining the incidence of gene amplification within a culture of said cells that is induced by contact with a first substance or process;
b. determining the incidence of gene amplification within a culture of reference cells that are not abnormally genetically labile, that is induced by contact with said first substance; and
c. comparing said incidence of induced gene amplification within the culture of cells with the incidence of induced gene amplification within the culture of reference cells to determine whether said cells are abnormally genetically labile, an induction of gene amplification in said cells greater than in the reference cells indicating abnormal genetic lability.

7. A method of claim 6 wherein the incidence of gene amplification within either culture of cells is determined by a process comprising the following steps:
a. dividing the cell culture into at least one first group of cells and at least one second group of cells;
b. contacting said first group with a first substance or process that is known to promote tumors or gene amplification;
c. contacting said first group and said second group with a second substance that kills cells which do not have a relatively high number of copies of at least one DNA locus that codes for the production of a protein that is the target of said second substance; and
d. determining the incidence of cells in each of said groups that survive the contact with said second substance to determine the incidence of gene amplification.

8. A method for indicating whether cells are abnormally genetically labile, comprising the following steps:
a. dividing a culture of said first cells into at least one first group and at least one second group;
b. contacting said first group with a first substance or process that is known to promote tumors or gene amplification;
c. contacting said first group and said second group with a second substance that kills cells which do not have a relatively high number of copies of at least one DNA locus that codes for the production of a protein that is the target of said second substance;
d. determining the number of cells in each of said first and second groups that survive the contact with said second substance;
e. comparing the incidence of surviving cells in each of said groups to determine the incidence of gene amplification within said cells;
f. dividing a popultion of reference cells that are not abnormally genetically labile into at least one third group and at least one forth group;
g. contacting said third group with said first substance or process;
h. contacting said third group and said fourth group with a said second substance;
i. determining the incidence of cells in each of said third and fourth groups that survive contact with said second substance;
j. comparing the incidence of surviving cells in each of said groups to determine the incidence of gene amplification within said reference cells; and
k. comparing the incidence of gene amplification within said first cells with the incidence of gene amplification within said reference cells to determine whether the cells are abnormal genetically labile.

9. A method of claim 8 wherein said second substance is selected from the following group: methotrexate, heavy metals, and phosphonacetyl-L-aspartate.

10. A method for indicating whether cells are abnormally genetically labile, comprising the following steps:
a. contacting a culture of said cells with a substance that kills cells which do not have a relatively high number of copies of at least one DNA locus that codes for production of a protein that is the target of said substance;
b. contacting a culture of reference cells that are not abnormally genetically labile with said substance;

c. determining the incidence of cells in each of said cultures that survive contact with said substance;

d. comparing said incidences to determine whether said cells are abnormally genetically labile, a higher rate of survival over the reference cells indicating genetic lability.

11. A method of claim 10 wherein said substance is selected from the following group: methotrexate, heavy metals, and phosphonacetyl-L-aspartate.

* * * * *